(12) United States Patent
Ho et al.

(10) Patent No.: US 8,169,617 B2
(45) Date of Patent: May 1, 2012

(54) METHOD AND APPARATUS FOR PHASE SENSITIVE SURFACE PLASMON RESONANCE

(75) Inventors: Ho Pui Ho, Hong Kong (CN); Siu Kai Kong, Hong Kong (CN); Yick Keung Suen, Hong Kong (CN); Kwong Chun Lo, Hong Kong (CN); Shu Yeun Wu, Hong Kong (CN); Wing Wai Wong, Hong Kong (CN)

(73) Assignee: The Chinese University of Hong Kong, Shatin, NT, Hong Kong (HK)

( * ) Notice: Subject to any disclaimer, the term of this patent is extended or adjusted under 35 U.S.C. 154(b) by 148 days.

(21) Appl. No.: 12/408,627

(22) Filed: Mar. 20, 2009

(65) Prior Publication Data

US 2009/0251707 A1    Oct. 8, 2009

Related U.S. Application Data

(60) Provisional application No. 61/041,776, filed on Apr. 2, 2008.

(51) Int. Cl.
 *G01B 9/02* (2006.01)
(52) U.S. Cl. ........................................ 356/453; 356/491

(58) Field of Classification Search .................. 356/445, 356/491, 492, 453
See application file for complete search history.

(56) References Cited

U.S. PATENT DOCUMENTS

| | | | |
|---|---|---|---|
| 6,277,330 B1 * | 8/2001 | Liu et al. | 422/82.05 |
| 6,943,893 B2 * | 9/2005 | Chou et al. | 356/484 |
| 7,473,917 B2 * | 1/2009 | Singh | 250/504 R |
| 2003/0030817 A1 * | 2/2003 | Lee et al. | 356/491 |
| 2007/0279635 A1 * | 12/2007 | Wu et al. | 356/445 |

OTHER PUBLICATIONS

Law et al. "Wide dynamic range phase-sensitive surface plasmon resonance biosensor based on measuring the modulation harmonics"; 2007; *Biosens Bioelectron.*; 12(5):627-32. (Epub Aug. 3, 2007).
Wu et al. "Highly sensitive differential phase-sensitive surface plasmon resonance biosensor based on the Mach-Zehnder configuration" 2004; *Opt Lett.*; 29(20):2378-80.

* cited by examiner

*Primary Examiner* — Hwa Lee
(74) *Attorney, Agent, or Firm* — Kilpatrick Townsend & Stockton LLP (57) ABSTRACT

There is disclosed a phase sensitive surface plasmon resonance sensing apparatus wherein a testing beam may be reflected from a sensing surface at a plurality of angles. There are also disclosed methods for surface plasmon resonance sensing.

14 Claims, 9 Drawing Sheets

METHOD AND APPARATUS FOR PHASE SENSITIVE SURFACE PLASMON RESONANCE

This application claims the benefit of U.S. Provisional Application No. 61/041,776 filed Apr. 2, 2008, the entire contents of which are hereby incorporated herein by reference.

FIELD

This disclosure relates to surface plasmon resonance (SPR) detection devices

BACKGROUND

A range of Surface Plasmon Resonance (SPR) techniques are known. Ho et al. from Chinese University of Hong Kong reported a phase-sensitive SPR sensor based on a Mach-Zehnder interferometer (Optics Letter, 29, 2378-2380, 2004). To provide a wider dynamic range, Law at al. proposed to measure the modulation harmonics in the phase-sensitive SPR system (Biosensors and Bioelectronics, 23, 627-632, 2007).

SUMMARY

There is disclosed a method and apparatus for phase-sensitive SPR.

In a first embodiment there is disclosed a phase sensitive SPR sensing apparatus comprising a sensing unit having a sensing surface to reflect a testing beam of electromagnetic radiation and wherein the testing beam is reflected from said sensing surface at a plurality of angles.

In alternative embodiments the range of illumination angles may be between about 0° and about 0°, about 10° and about 20°, about 20° and about 30°, about 30° and about 40°, about 40° and about 50°, about 50° and about 60°, 60° and about 70°, about 70° and about 80°, about 80° and about 90°.

In alternative embodiments, the apparatus may further comprise a detecting unit to detect said reflected beam at least two of said reflected angles.

In alternative embodiments, the apparatus may further comprise a plurality of detectors.

In alternative embodiments, the detecting unit compares the phase of said reflected testing beam with the phase of a reference beam.

In alternative embodiments, the reference beam and said testing beam are generated by a beam splitter.

In alternative embodiments, the apparatus may further comprise a focussing unit to focus said testing beam.

In alternative embodiments, the focussing unit comprises a cylindrical lens.

In alternative embodiments, the apparatus may further comprise a beam converging unit, for converging the said testing beam.

In alternative embodiments, the apparatus may further comprise a detection unit comprising a photodetector array.

In alternative embodiments, the apparatus may further comprise a detection unit comprising a phase meter.

In alternative embodiments, the apparatus may further comprise a source of said first beam comprising a liquid crystal modulator.

In alternative embodiments, the apparatus may further comprise a source of polarised electromagnetic radiation with variable phase retardation.

In alternative embodiments, the detection unit may comprise a polarizer, a photodetector detecting interfered electromagnetic radiation from said polariser, and a processor for comparing the phase pattern of the interfered electromagnetic radiation and the reference beam.

In alternative embodiments, the source of said first beam comprises a gas laser, a solid state laser, a laser diode, a light emitting diode or a diode laser.

In alternative embodiments, the sensing unit further comprises a prism and a sample flow system for allowing the sample flow over the sensing surface.

In alternative embodiments, the sensing unit comprises a transducing layer and the transducing layer is either a metal layer suitable to perform conventional SPR effect or metal/dielectric layer/metal configuration.

In alternative embodiments there is disclosed a sensing apparatus comprising a source of electromagnetic radiation, a beam splitter to generate a testing beam and a reference beam, a sensing surface, a electromagnetic radiation focusing unit, to focus said testing beam on said sensing surface at a plurality of angles, a detection unit, for detecting the differential phase change between said reference beam and said reflected testing beam.

In alternative embodiments the range of illumination angles is between about 0° and about 0°, about 10° and about 2°, about 20° and about 30°, about 30° and about 40°, about 40° and about 50°, about 50° and about 60°, 60° and about 70°, about 70° and about 80°, about 80° and about 90°.

In alternative embodiments the detection unit comprises a plurality of detectors.

In alternative embodiments the detection unit comprises a detector array.

In alternative embodiments the detection unit comprises a phase meter for measuring a differential phase of each point of output signal array.

In alternative embodiments the source further comprises a polarizer for selecting an intensity ratio between the p- and s-polarization components of the emitted electromagnetic radiation.

In alternative embodiments the detecting unit further comprises a polarizer and a photodetector and is adapted to compare the phase of said testing beam and said reference beam.

In alternative embodiments the focusing unit comprises a beam expander for expanding the testing beam diameter; a lens for focussing the beam onto the sensing surface.

In alternative embodiments the sensing unit comprises a prism and a sample flow chamber to permit a sample to flow through the sensing surface.

In alternative embodiments the source comprises a phase modulator.

In alternative embodiments the unit comprises a gas laser, a solid state laser, a laser diode, or a light emitting diode.

In alternative embodiments there is disclosed a method for SPR sensing, said method comprising reflecting a testing beam off a testing surface from a plurality of illumination angles; detecting the phase of said reflected beam; and comparing the phase in the reflected testing beam against the phase of said reference beam to characterize said sample.

In alternative embodiments the method further comprises detecting the change in phase of said reflected beam.

In alternative embodiments the reflected beam is compared against a reference beam.

In alternative embodiments the testing beam is substantially parallel when incident on said sensing surface.

In alternative embodiments the comparing comprises forming an interference between p- and s-polarization components of the reference beam; detecting the interfered electromagnetic radiation; and comparing the phase in said interfered electromagnetic radiation against the phase of said testing beam.

In alternative embodiments the range of illumination angles is between about 0° and about 0°, about 10° and about 20°, about 20° and about 30°, about 30° and about 40°, about 40° and about 50°, about 50° and about 60°, 60° and about 70°, about 70° and about 80°, about 80° and about 90°.

In alternative embodiments the first beam is generated by a gas laser, a solid state laser, a laser diode, or a light emitting diode.

In alternative embodiments the electromagnetic radiation may be light.

In alternative embodiments the electromagnetic radiation may be visible light.

Features and advantages of the subject matter disclosed will become more apparent in light of the following detailed description of some embodiments thereof, as illustrated in the accompanying figures. As will be realized, the various embodiments are capable of modifications in various respects and may be combined in a variety of alternative ways, all without departing from the spirit and scope of the claims. Accordingly, the drawings and the description are to be regarded as illustrative in nature, and not as restrictive.

DETAILED DESCRIPTION OF EMBODIMENTS

Definitions

In this disclosure, the word "comprising" is used in a non-limiting sense to mean that items following the word are included, but items not specifically mentioned are not excluded. A reference to an element by the indefinite article "a" does not exclude the possibility that more than one of the elements is present, unless the context clearly requires that there be one and only one of the elements.

In this disclosure the recitation of numerical ranges by endpoints includes all numbers subsumed within that range including all whole numbers, all integers and all fractional intermediates (e.g., 1 to 5 includes 1, 1.5, 2, 2.75, 3, 3.80, 4, and 5 etc.).

In this disclosure the singular forms "a", "an", and "the" include plural referents unless the content clearly dictates otherwise. Thus, for example, reference to a composition containing "a compound" includes a mixture of two or more compounds.

In this disclosure the term "or" is generally employed in its sense including "and/or" unless the content clearly dictates otherwise.

In this disclosure, unless otherwise indicated, all numbers expressing quantities or ingredients, measurement of properties and so forth used in the specification and claims are to be understood as being modified in all instances by the term "about". Accordingly, unless indicated to the contrary or necessary in light of the context, the numerical parameters set forth in the disclosure are approximations that can vary depending upon the desired properties sought to be obtained by those skilled in the art utilizing the teachings of the present disclosure and in light of the inaccuracies of measurement and quantification. Without limiting the application of the doctrine of equivalents to the scope of the claims, each numerical parameter should at least be construed in light of the number of reported significant digits and by applying ordinary rounding techniques. Not withstanding that the numerical ranges and parameters setting forth the broad scope of the disclosure are approximations, their numerical values set forth in the specific examples are understood broadly only to the extent that this is consistent with the validity of the disclosure and the distinction of the subject matter disclosed and claimed from the prior art.

In this disclosure the term "dielectric" has its ordinary meaning and includes materials such as glass, polymers, ceramics, silicon nitride, silicon dioxide and any materials with dielectric properties suitable for use in.

In this disclosure the term "source" or "source of electromagnetic radiation" may comprise an electromagnetic radiation emitter which may comprise a gas laser, a solid state laser, a laser diode, a light emitting diode (LED), a broad band source of electromagnetic radiation or any other suitable electromagnetic radiation emitter. In embodiments the source of electromagnetic radiation (also referred to herein as simply a "source") may be or may comprise a linear polarization He—Ne laser. In particular embodiments the source of electromagnetic radiation may have an optical output power of about 12 mW but in alternative embodiments may have an output power of greater than about 1 mW, 2 mW, 4 mW, 6 mW, 8 mW, 10 mW, 12 mW, 14 mW, 16 mW, 20 mW, 22 mW, 24 Mw, 26 mW, 28 mW, 30 mW, 40 mW, 50 mw or more. The radiation emitter may emit a beam of light containing s- and p-polarization components and the polarization of the output light beam may be set offset from the p-polarization at a polarisation angle α which may be about 45°. In embodiments the polarisation angle α may be greater or less than about 45° and will be readily adjusted by those skilled in the art to suit specific requirements. In embodiments the polarisation angle may be up to about 5°, 10°, 15°, 20°, 25°, 30°, 35°, 40°, 45°, 50°, 55°, 60°, 65°, 70°, 75°, 80°, 85°, or 90°. In embodiments some choices of polarisation angle may reduce the amplitude of the s- and p-polarization components and may degrade the phase detection capability of the system. It will be understood that in embodiments a source of electromagnetic radiation may comprise additional devices, including but not limited to, optical fibers, lenses and/or mirrors for focusing, collimating, polarizing, filtering, aiming and/or altering the properties of the light beam.

In this disclosure the term "electromagnetic radiation" may comprise any of a range of wavelengths of electromagnetic radiation, which will be readily selected between by those skilled in the art for use in particular embodiments. Without limitation the foregoing, in particular embodiments electromagnetic radiation may include light, and may include visible light, ultraviolet light, infrared light, X-ray, gamma ray, polarized radiation and radio waves.

In this disclosure the term "photodetector" means a device for detecting incident electromagnetic radiation and may include charge coupled devices, charge injection devices, cameras, photo diodes, photomultipliers, CMOS sensors, photographic film, light sensing diodes, and may include arrays or multichannel arrangements of any of the foregoing.

In this disclosure the term "beam splitter" means a device for splitting an incident beam of electromagnetic radiation into two or more output beams. In embodiments a beam splitter may comprise a glass slide or equivalent surface positioned at an angle to the incident beam.

In this disclosure the term "sensing unit" means an apparatus for accepting a sample to be tested using embodiments and may comprise suitable reflective surfaces, prisms, sample holding chambers, and means for allowing sample or solutions of sample to be held in or passed through the sensing unit.

In this disclosure the term "detecting unit" or "detection unit" means an apparatus for detecting electromagnetic radiation and may comprise a processor for processing information concerning such detected electromagnetic radiation. In embodiments a detecting unit may further comprise apparatus for comparing electromagnetic radiation from different sources, including reference and testing beams, and may comprise photodetectors, arrays of photodetectors, and may comprise processing apparatus for processing information relating to electromagnetic radiation detected. In embodiments the detecting unit may detect polarised electromagnetic radiation and may compare elements of polarised light in two or more received beams of electromagnetic radiation.

In this disclosure "SPR" means Surface Plasmon Resonance, and includes but is not limited to Long Range Surface Plasmon Resonance (abbreviated herein as "LRSPR").

In this disclosure the terms "SPR sensing unit" and "SPR sensor" and like terms may, in particular embodiments, comprise Kretschmann and Otto configurations, may comprise arrays of lenses or microlenses, and may comprise either prism or grating or diffraction configurations. In embodiments prisms may have a high refractive index range and may have an n of between about 0.9 and about 2.5, or less than about 0.9 or more than about 2.5, or between about 1.0 and 2.0, or between about 1.1 and 1.9, or between about 1.2 and 1.8, or between about 1.3 and 1.8 or between about 1.4 and 1.7. In particular embodiments and where the prism comprises silicon n may take a value of between 3.4 and 3.5.

In this disclosure a "conductor" or "conducting layer" or the like, includes conductive materials able to support a surface plasmon, and may include metals with free electrons, and may comprise or consist of gold, silver, platinum, nickel, copper, chromium, or aluminum but is not limited to such components. Suitable selections will be readily made by those skilled in the art.

The embodiments are described with general reference to FIGS. 1 through 10. In a first embodiment there is disclosed a phase sensitive SPR sensing apparatus generally designated 10 comprising a sensing unit 400 having a sensing surface 402 to reflect a testing beam 920 of electromagnetic radiation and wherein the testing beam is reflected from said sensing surface at a plurality of angles. In embodiments the range of illumination angles may be between about 0° and about 0°, about 10° and about 20°, about 20° and about 30°, about 30° and about 40°, about 40° and about 50°, about 50° and about 60°, 60° and about 70°, about 70° and about 80°, about 80° and about 90°. In embodiments the apparatus may further comprise a detecting unit 600 (also alternatively referred to as a detection unit or as a probe unit) to detect said reflected beam 930 at least two magnitudes of said reflected angle γ and may comprise a plurality of detectors.

In alternative embodiments, the detecting unit 600 may compare the phase of said reflected testing beam 910 with the phase of a reference beam 900. The reference beam 900 and testing beam 930 may be generated by a beam splitter 104. The apparatus may further comprise a focussing unit (alternatively referred to as a beam converging unit) generally designated 300 to focus testing beam 910. The beam converging unit 300 may comprise a cylindrical lens and the apparatus may further comprise a beam expander 301, for converging the testing beam 910. The detecting unit 600 may comprise a photodetector array 502 and may comprise a phase meter. In embodiments, the apparatus may further comprise a source 100 of said first beam 800 comprising a liquid crystal modulator 109 and in further embodiments the source 100 of polarised light may be capable of variable phase retardation.

In embodiments, the detecting unit 600 may comprise a polarizer 102 and may comprise a photodetector for detecting interfered light from said polariser, and a processor for comparing the phase pattern of the interfered light and the reference beam. In particular embodiments the source 100 of said first beam may comprise a gas laser, a solid state laser, a laser diode, a light emitting diode or a diode laser. The sensing unit may further comprise a prism having sensing surface 402; and a sample flow system 403 for allowing the sample flow over the sensing surface. In alternative embodiments the transducing layer may be either a metal layer suitable to perform conventional SPR effect; or a metal/dielectric layer/metal configuration. In embodiments converging unit 300 may comprise a cylindrical lens and may comprise a lens 302

The first embodiment is now described in greater detail with reference to the drawings.

Figure 1:
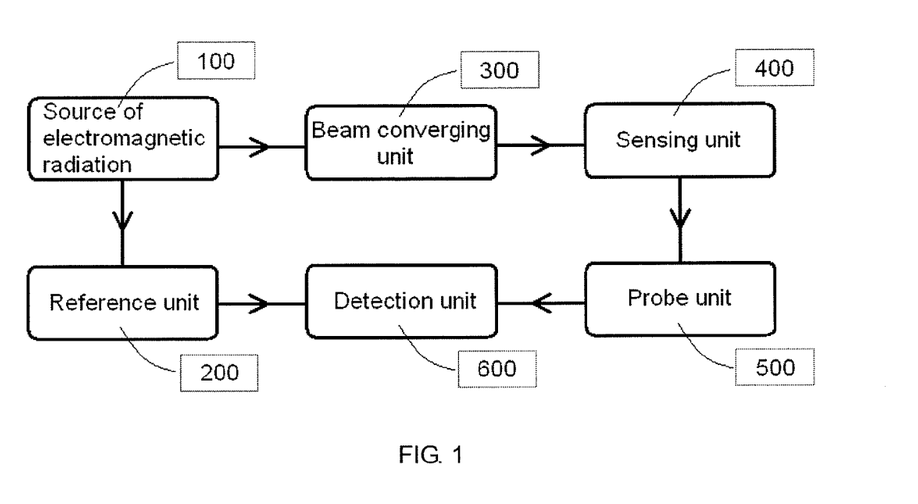
FIG. 1 is a block diagram of a wide dynamic range phase-sensitive SPR biosensor according to a first embodiment.

FIG. 1 illustrates a wide dynamic range phase-sensitive SPR and LRSPR (Long Rang Surface Plasmon Resonance) sensor. The SPR sensor may comprise: a source of electromagnetic radiation 100 which may comprise an electromagnetic radiation emitter 101. Source 100 may be an optical light source for providing a beam 800 of light containing p- and s-polarization components with a modulated phase retardation between the p- and s-polarization components; a reference unit 200 for receiving one portion of the beam to provide a reference signal indicating the modulated phase retardation; a beam converging or focussing unit 300 for charging the parallel beam to converging beam; a sensing unit 400 for receiving another portion of the beam to induce a phase retardation chance between the p- and s-polarization components due to SPR or LRSPR associated with a sample; an optical detector array unit 500 for receiving the light passing the SPR sensing unit so as to provide a set of signal traces for computing the phase retardation change induced by the SPR sensing unit; and a detection unit (also referred to as a detecting unit or probe unit) 600 connected to the reference unit to compute the reference retardation baseline so that the actual SPR-induced retardation can be found from subtracting the reference retardation from the one obtained from the optical detector array unit. It will be noted that the detecting unit 600 may be associated with or may comprise a photodetector or photodetector array 502/500.

Figure 2:
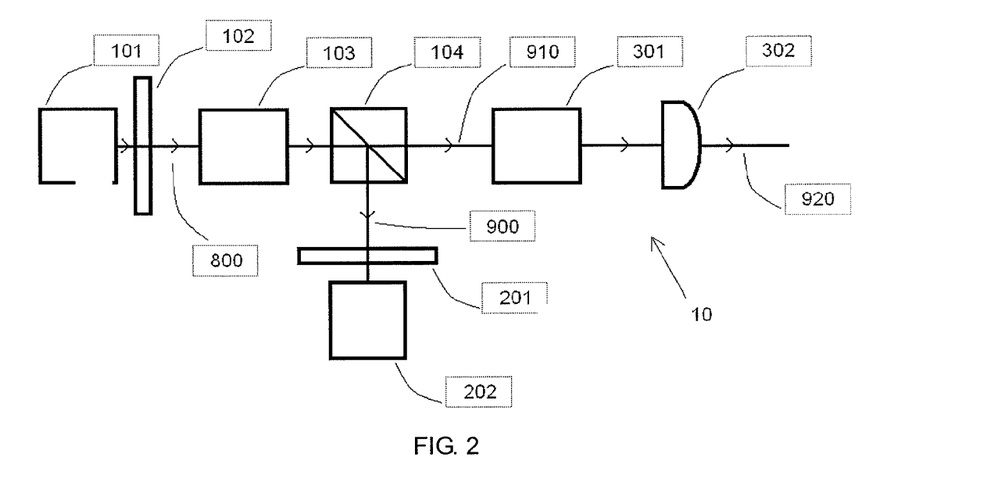
FIG. 2 is a schematic view of a source of electromagnetic radiation, a reference unit and beam converging unit according to a first embodiment.

As shown in FIG. 2, the source of electromagnetic radiation 100 may comprise an electromagnetic radiation emitter 101, a polarizer 102, a liquid crystal phase modulator 103, and a beam splitter 104.

In an embodiment the electromagnetic radiation emitter 101 comprises a gas laser. In alternative examples it may comprise a solid state laser, a laser diode, a light emitting diode (LED) or any other suitable electromagnetic radiation emitter. The radiation emitter 101 generates a beam of light containing p- and s-polarization components. In an embodiment a linear polarization He—Ne laser with optical output power of 12 mW is employed and its polarization may be set at 450 off the p-polarization.

The polarizer 102 may be provided to select a content ratio between p- and s-polarization components of the source of electromagnetic radiation by rotating a polarization angle of the polarizer 102. In embodiments the polarization angle of the polarizer 102 may be set at 45° off to the p-polarization optical axis to obtain an equal content in both p- and s-polarization components.

Figure 3:
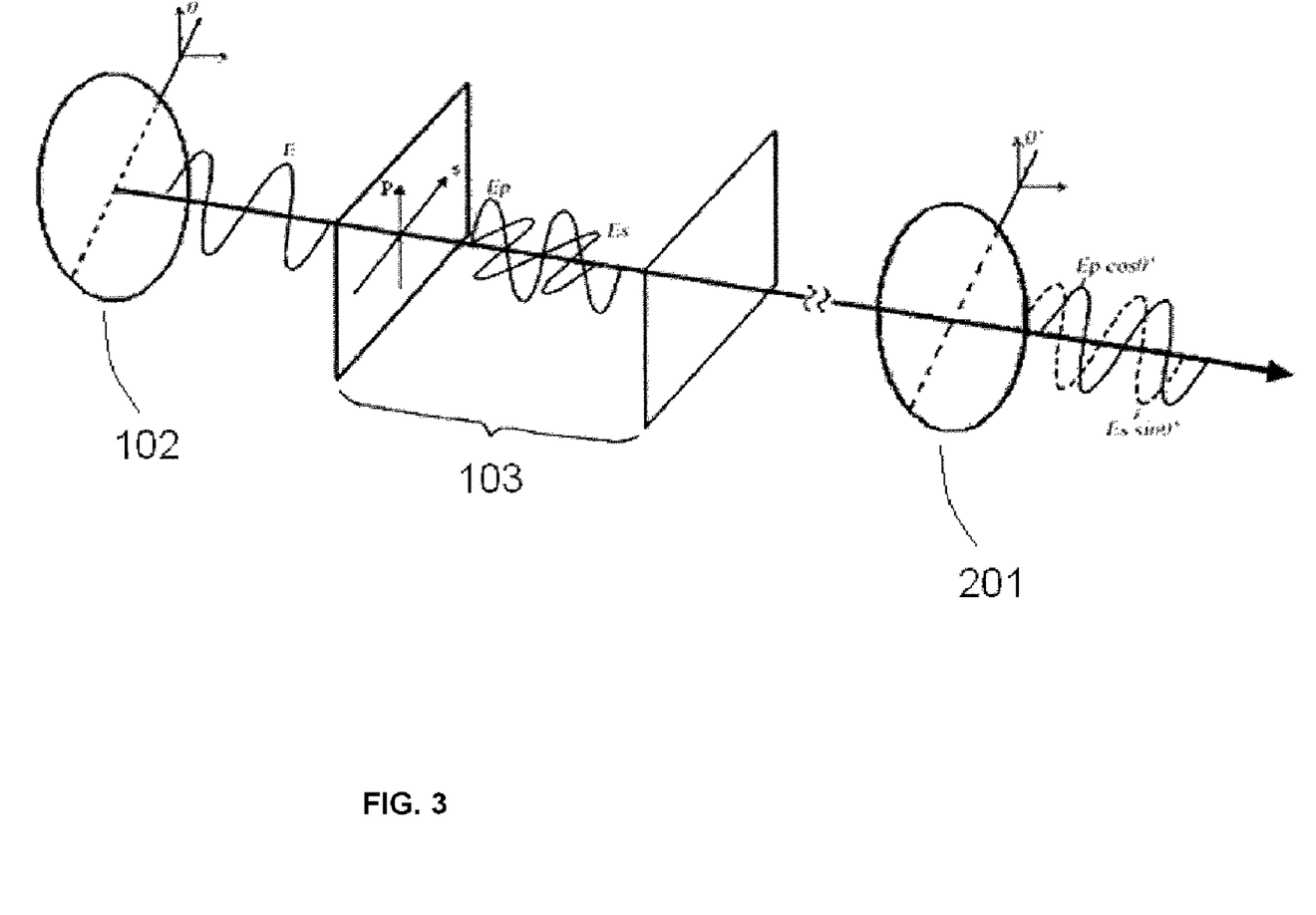
FIG. 3 is a schematic view showing the operation principle of a liquid crystal modulator according to the embodiment of FIG. 1.

The phase modulator 103 may be a liquid crystal modulator (LCM) for modulating the optical phase retardation between the p- and s-polarization components. The modulation principle is described as shown in FIG. 3. The LCM 103 receives the light passing through the polarizer 102. A periodic drive voltage may be applied to LCM 103 to induce a phase retardation θ to the p- and s-polarization components after the light passes through it. According to this example of an embodiment, the modulation depth of the LCM 103 may be about 0 to 9π and the frequency of the LCM 103 may be set to be about 30 Hz. In alternative embodiments the modulation depth may be up to about 1π, 2π, 3π, 4π, 5π, 6π, 7π, 8π, 9π, 10π, 11π, 12π, 13π, 14π, 15π, 20π, 25π, 30π or greater than 30π. In alternative embodiments the frequency of the LCM may be set at up to about 10 Hz, 20 Hz, 30 Hz, 40 Hz, 50 Hz, 60 Hz, 70 Hz, 80 Hz, 90 Hz, 100 Hz, 1 kHz, 10 kHz, 100 kHz, 1 MHz, 10 MHz, 100 MHz, 1 GHz, 10 GHz, 100 GHz, or greater. Depending on the characteristics of the LCM other modulation depths and frequencies may used and all will be readily recognised and implemented by those skilled in the art to suit specific requirements.

A beam splitter 104, which may be a blank glass slide, may be used to separate the beam of light into two parts. One resulting beam may be a probe or testing beam 910 and the other may be a reference beam 900. The reference beam 900 can be generated by the reference unit 200 which comprises a polarizer 201 and a photodetector 202. As shown in FIG. 2, the polarizer 201 may be set to a polarization angle α that can generate interference between the p- and s-polarization components of the reference beam. In particular embodiments the polarization angle α may be any suitable angle, all of which will be readily identified by those skilled in the art, in particular embodiments the polarization angle α may be about 45° or may be greater than or less than 45° depending on the specific requirements of the user. The photodetector 202 may be used for converting the optical intensity variation to an electrical signal while the LCM continuously sweeps the retardation difference between the p- and s-polarization components. In this example photodetector 202 may be a photodiode.

In the beam converging unit 300 (also referred to as a focussing unit), a beam expander 301 may first expand the beam diameter of the testing beam and a lens 302 may then focus the beam to form a beam of light 920 covering a range of illumination angles. This line of optical beam reaches its focal point at the sensing surface 302 of the SPR system and it begins to diverge after reflection. As SPR occurs only in a narrow range of incident angles, this arrangement ensures that the illumination covers a wide range of conditions, including those concerned with before and after resonance. The resolution of the incident angle depends on the number of pixels in the photodetector array 502 and the angle of acceptance of the SPR sensing surface 402.

In an embodiment said range of incident angles may be between about 60° and about 70°. It will be appreciated that in embodiments the range of incident angles may be anywhere between the critical angle of total internal reflection of the sensing layer and 90°. In alternative embodiments, the angle may be between about 50° and 70°, between about 55° and 750, between about 50° and 80°, between about 45° and 850, between about 40° and 900. In embodiments it may include angles greater than about 80° or less than about 10°. In embodiments the angle may be greater than about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170 or more degrees or may be less than about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165 or 170 degrees. In embodiments the angle may be between about 0° and about 0°, about 10° and about 20°, about 20° and about 30°, about 30° and about 40°, about 40° and about 50°, about 50° and about 60°, 60° and about 70°, about 70° and about 80°, about 80° and about 90°.

Figure 4:
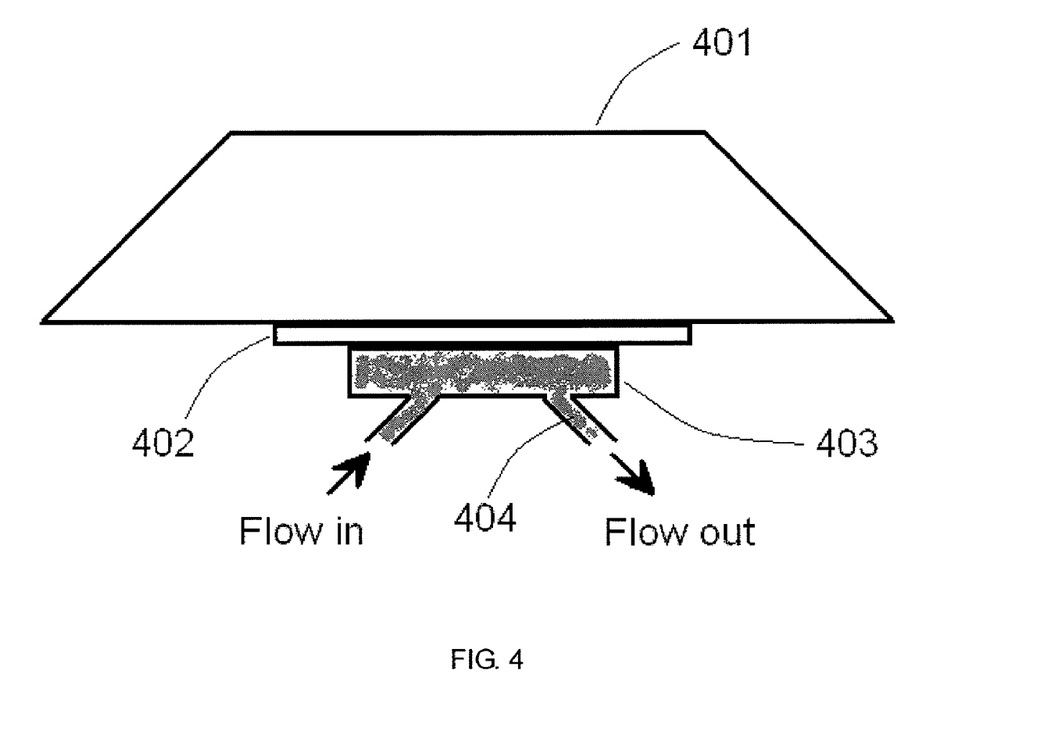
FIG. 4 is a schematic view of a conventional SPR sensing surface configuration.
Figure 5:
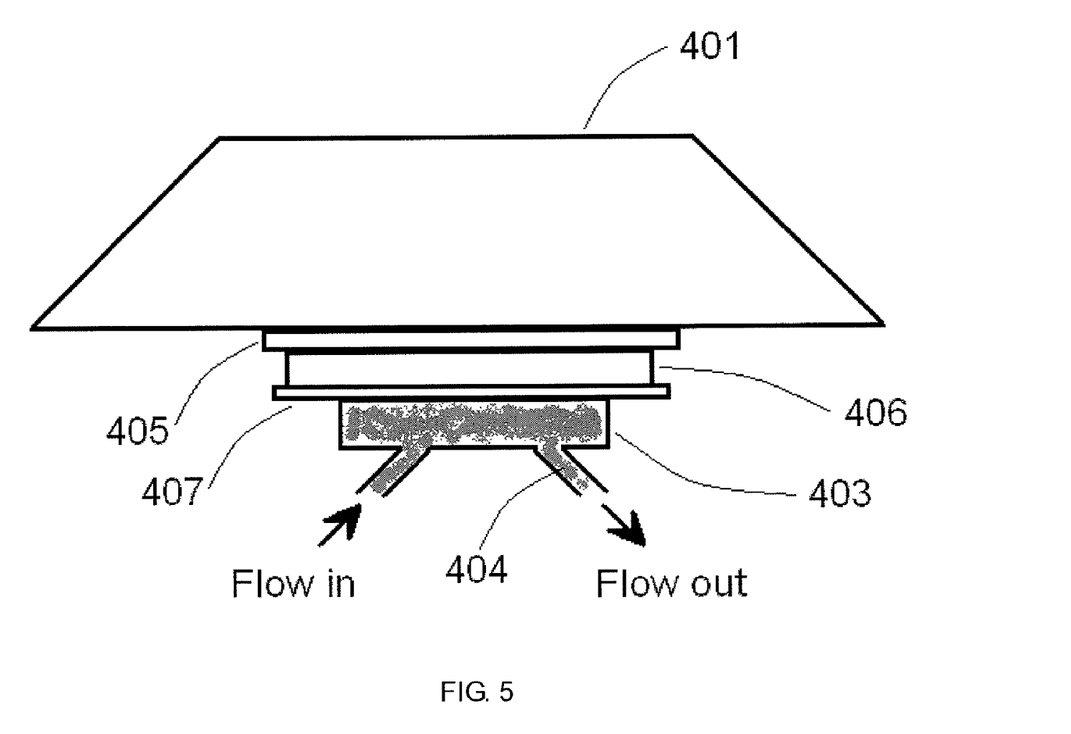
FIG. 5 is a schematic view of a LRSPR sensing surface configuration according to an embodiment.

For the sensing unit 400, a prism coupling scheme for conventional SPR configuration (prism/metal layer/sample) and LRSPR configuration (prism/metal layer/dielectric layer/metal layer/sample) are used and the configurations thereof are shown in FIG. 4 and FIG. 5 respectively. In those configurations, the prism coupling scheme may comprise a prism 401, a sensing surface 402 on the prism 401, and a sample flow chamber 404 associated with the prism 401 for guiding a sample 403 flowing over the sensing surface 402. In embodiments the prism 401 can be made of transparent dielectric material such as plastic or glass in order to enhance the momentum of light to match with the momentum of SPR. In embodiments a dove prism made of BK7 glass may be employed. In the conventional SPR configuration, the transducing layer of the sensing surface 402 may be commonly made of conducting material such as gold or silver. A range of other metals may be useable, and for instance but without limitation, in embodiments the conducting surface may comprise or consist of platinum, nickel, copper, aluminum, or chromium, and in embodiments the sensing surface may overlay a different metal or other conducting layer or a dielectric.

In embodiments a gold layer, nominally 48 nm thick, may be employed because of its good chemical resistance. The thickness of such a layer may be in the range of 20 nm to 80 nm depending on applications and material selection. In embodiments the thickness may be anywhere between 0.1 and 1 nm, 1 and 2 nm, 2 and 5 nm, 5 and 10 nm, 10 and 20, 20 and 30, 30 and 40, 40 and 50, 50 and 60, 60 and 70, 70 and 80, 80 and 90, 90 and 100, 100 and 110, 110 and 120, 120 and 140, 140 and 180, 180 and 220 nm or greater than 220 nm.

In LRSPR configuration, the transducing layer of the sensing surface 402 may be made of a dielectric layer 406 which may be sandwiched by two conducting material layers 405 and 407 FIG. 5. In an embodiment the conducting layers may comprise gold or silver. In an embodiment, the first layer of the conducting material forming the prism surface may be gold with a thickness of 48 nm. The second layer of the dielectric material may be silicon dioxide with a thickness of 453 nm. The third layer of the conducting material may be gold with a thickness of 2 nm. The choice of thickness for the layers may be modified for particular applications and material selection, dimensions and the like will be readily modified by those skilled in the art to suit particular requirements. In embodiments the sample 403 may be used in aqueous form. In one embodiment glycerin and water mixtures may be used in the concentration of weight percentage from 0% to 8% with 1% increments. The sample flow chamber 404 may be designed to permit the sample 403 flowing in and out of the chamber 404 while making contact with the sensing surface.

In the optical detector array unit 502/500, a polarizer 501 may be oriented so that the p- and s-polarization components of the probe beam can interfere with each other. Then an optical detector array 502 may be used to capture the optical intensity variations of the diverging probe beam at difference angle of incidence. The signal trace from each of the optical detector element may contain all the information required for computing the phase change associated with the SPR effect at a specific incident angle.

Figure 6:
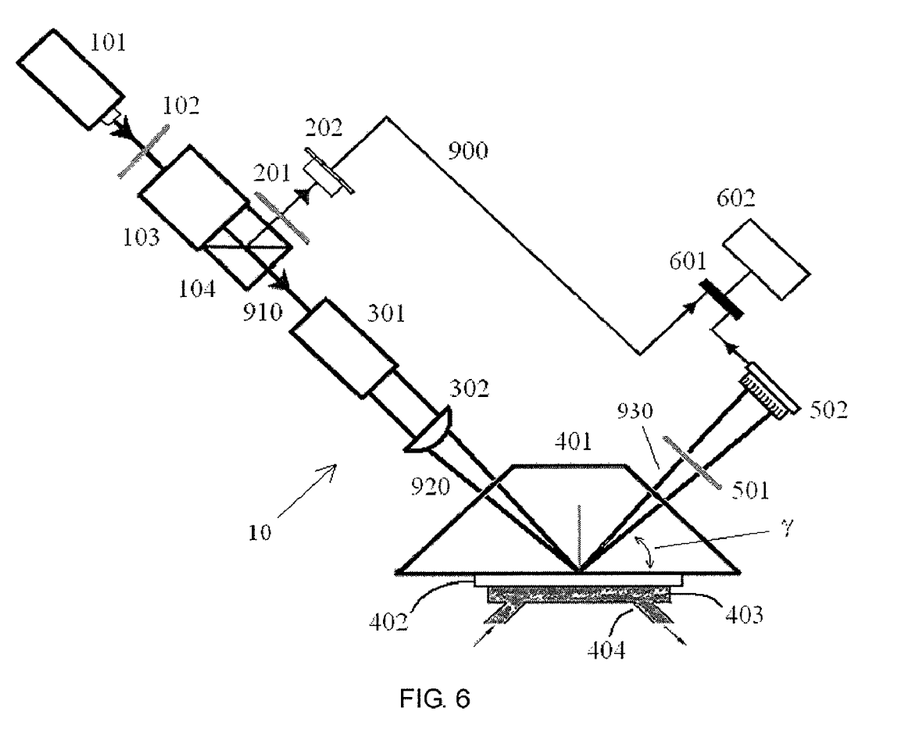
FIG. 6 is a schematic view of a SPR sensor according to an embodiment.

As shown in FIG. 6, the detection unit 600, which may be connected between the reference unit 200 and the optical detector array unit 500/502 and may comprise the optical detector array 500, may comprise a phase meter 601 and a microprocessor 602. The phase meter 601 may be employed to measure a differential phase between the reference channel and the probe channel so that the differential phase and subsequently the refractive index change associated with the binding of biomolecules or other molecules to be analysed, to the sensor surface can be found using a microprocessor 602.

It will be understood that performance may be determined by, or may be affected by, a compromise between the numerical aperture of the optical light beam and the pixel count of the optical detector array. In embodiments a higher detector element count in the array may offer better resolution. But this may also mean the time required to complete a measurement will increase because the system has to process a larger number of signal traces.

It will be understood that in alternative embodiments one or more individual components of the apparatuses described may be combined or comprised in one another.

Alternative Embodiments:
In alternative embodiments there is disclosed a method for SPR sensing. The method may comprising reflecting a testing beam off a testing surface from a plurality of illumination angles, detecting the phase of said reflected beam and, comparing the phase in the reflected testing beam against the phase of said reference beam to characterize said sample. In embodiments the method may further comprise detecting the change in phase of said reflected beam, comparing the reflected beam against a reference beam. In embodiments the testing beam may be substantially parallel when incident on said sensing surface. In alternative embodiments the comparing between the reflected and reference beams may comprise forming an interference between p- and s-polarization components of the reference beam; detecting the interfered light; and comparing the phase in said interfered light against the phase of said testing beam.

In alternative embodiments there is disclosed a sensing apparatus comprising: a source of electromagnetic radiation; a beam splitter to generate a testing beam and a reference beam; a sensing surface; a light focusing unit, to focus said testing beam on said sensing surface at a plurality of angles; a detection unit, for detecting the differential phase change between said reference beam and said reflected testing beam.

Figure 7:
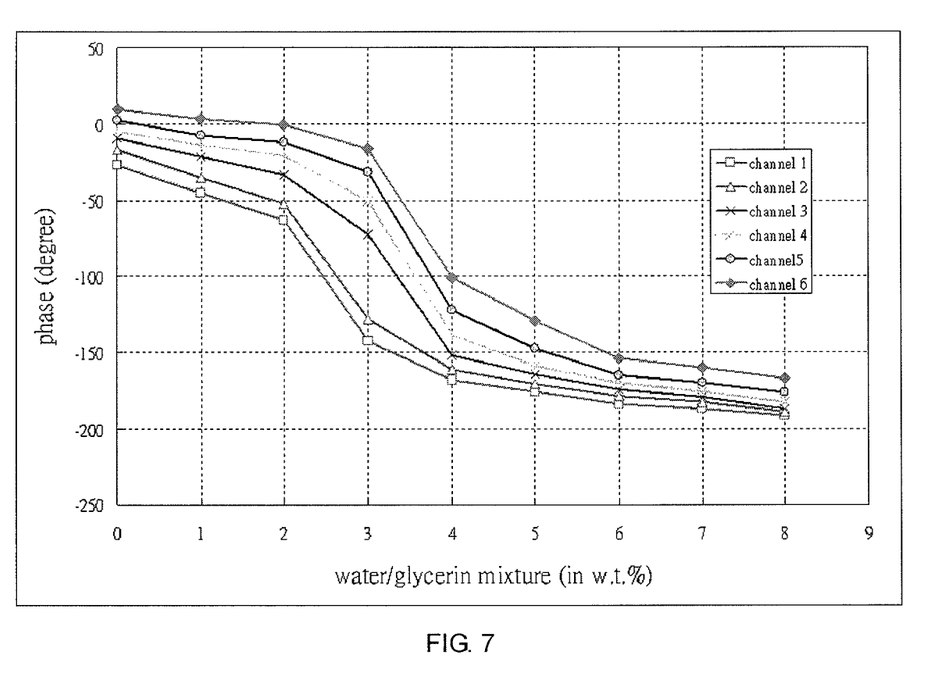
FIG. 7 shows the experimental result of a wide dynamic range phase-sensitive SPR sensor with conventional SPR sensing surface configuration obtained from glycerin and water mixtures.
Figure 8:
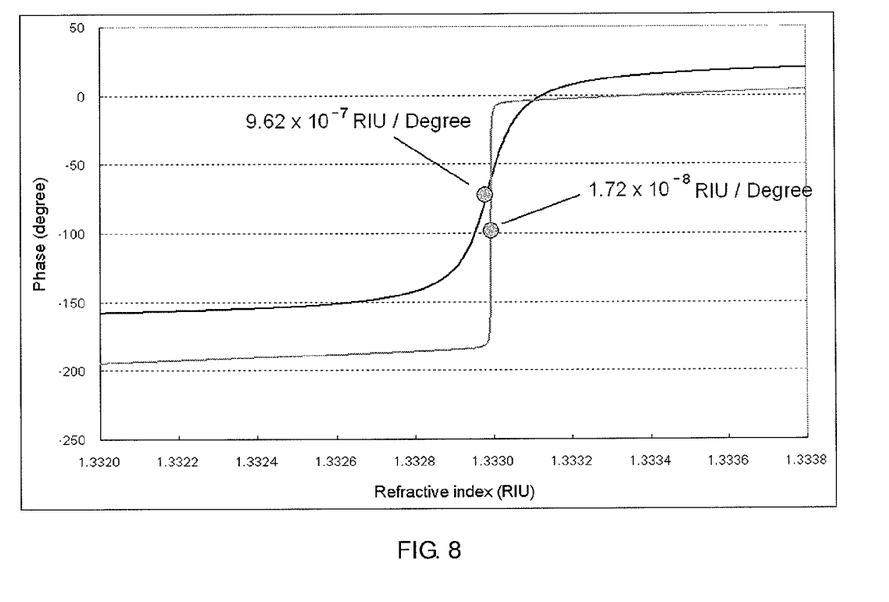
FIG. 8 shows simulated results of the phase response in conventional SPR and LRSPR sensing surface configurations.
Figure 9:
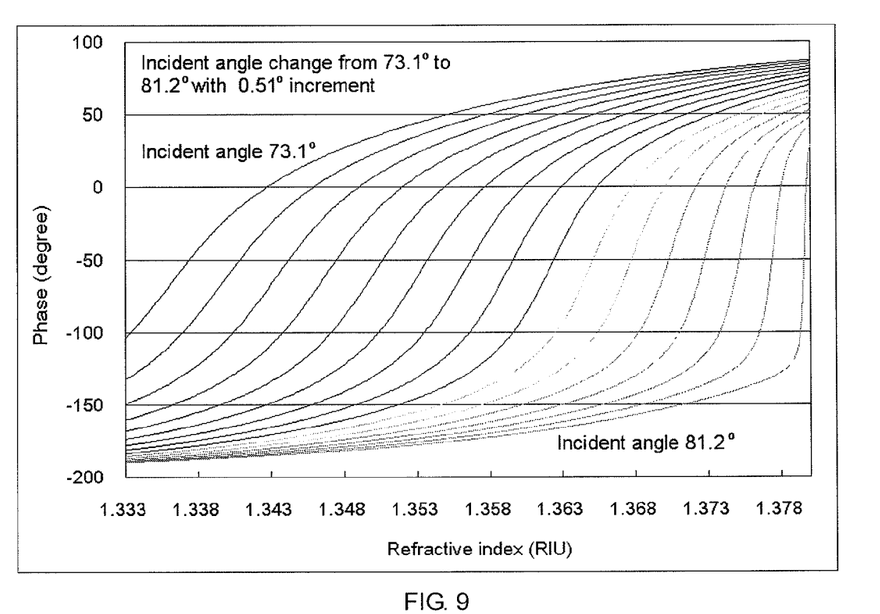
FIG. 9 shows the simulated results of the phase response in the wide dynamic range phase-sensitive SPR sensor with a conventional SPR sensing surface configuration.
Figure 10:
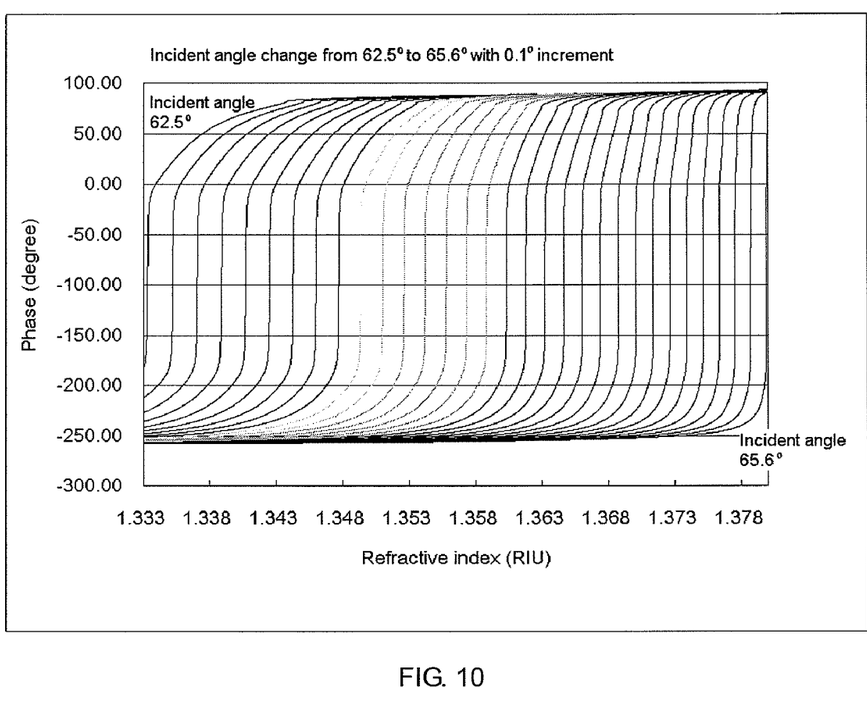
FIG. 10 shows the simulated results of the phase response in the wide dynamic range phase-sensitive SPR sensor using a LRSPR sensing surface configuration.

Examples of Embodiments:
To demonstrate the performance of an embodiment, an experiment using a conventional SPR sensing surface has been conducted. The test samples were mixtures of glycerin and water. The concentrations of these mixtures were from 0% to 8% in weight percentage with the corresponding refractive index unit (RIU) ranging from 1.3330 to 1.3424. The corresponding results are shown in FIG. 7. As seen from this plot, the system covers a dynamic range of $1\times10^{-2}$ RIU when the optical detector array contains only 6 elements. Simulation results on the phase responses from the conventional SPR and the LRSPR configurations are shown in FIG. 8. The sensor layer structures are a thin gold layer with 48 nm thickness for the conventional SPR configuration and a gold/silicon dioxide/gold multi-layer stack with thicknesses of 48 nm, 453 nm and 2 nm respectively for the LRSPR configuration. The results indicate that for a 1° phase change the corresponding refractive changes are $9.62\times10^{-7}$ for the conventional SPR configuration and $1.72\times10^{-8}$ RIU for the LRSPR configuration. FIG. 9 and FIG. 10 show simulation results of the phase response from the conventional SPR and LRSPR configurations when they are incorporated in the wide dynamic range phase-sensitive SPR sensor respectively. The incident angles used in this simulation cover a range of 62.500° to 65.627°, and the resultant signal traces are detected by a 16-element optical detector array for the conventional SPR configuration and 32-element optical detector array for the LRSPR configuration. The curves represent the phase response of the sensing layer at each illumination angle, which is the phase signal detected in each channel within the detector array. The phase response curve from the conventional SPR configuration is shown in FIG. 9, the refractive index sensing range is from 1.333 RIU to 1.38 RIU (i.e. the dynamic range is approximately $5\times10^{-2}$ RIU). The resolution gradually decreases from $2.92\times10^{-6}$ RIU/degree to $7.67\times10^{-5}$ RIU/degree as the refractive index moves further away from the optimized value. The phase response of the LRSPR configuration, as shown in FIG. 10, indicates that the resolution only varies from $2.14\times10^{-8}$ RIU/degree to $6.57\times10^{-8}$ RIU/degree within the dynamic range of $5\times10^{-2}$ RIU.

The embodiments and examples presented herein are illustrative of the general nature of the subject matter claimed and are not limiting. It will be understood by those skilled in the art how these embodiments can be readily modified and/or adapted for various applications and in various ways without departing from the spirit and scope of the subject matter disclosed and claimed. The claims hereof are to be understood to include without limitation all alternative embodiments and equivalents of the subject matter hereof. Phrases, words and terms employed herein are illustrative and are not limiting. Where permissible by law, all references cited herein are incorporated by reference in their entirety. It will be appreciated that any aspects of the different embodiments disclosed herein may be combined in a range of possible alternative embodiments, and alternative combinations of features, all of which varied combinations of features are to be understood to form a part of the subject matter claimed.

The invention claimed is:
1. An apparatus for SPR or for LRSPR comprising:
(1) a source of a testing beam of phase modulated electromagnetic radiation;
    wherein said source comprises a liquid crystal phase modulator; and
    a beam splitter to generate a testing beam and a reference beam;
(2) a converging unit to converge the testing beam;
    wherein said liquid crystal phase modulator is aligned with said converging unit such that said converging unit converges said testing beam onto said sensing surface over a plurality of illumination angles and

(3) a sensing unit for reflecting the testing beam from a sensing surface.

2. The apparatus according to claim 1 further comprising a detecting unit for detecting said reflected testing beam over a plurality of reflected angles.

3. The apparatus according to claim 2 wherein said detecting unit compares the phase of said reflected testing beam with the phase of a reference beam.

4. The apparatus according to claim 1 wherein said range of illumination angles is between about 10° and about 90°.

5. The apparatus according to claim 2 wherein said detecting unit comprises a photodetector array.

6. The apparatus according to claim 3 wherein said reference beam and said testing beam are generated by a beam splitter.

7. The apparatus according to claim 1, wherein said source of said testing beam comprises a gas laser, a solid state laser, a laser diode, a light emitting diode or a diode laser.

8. The apparatus according to claim 1, wherein said sensing unit further comprises:
a sample flow system for allowing the sample flow over the sensing surface.

9. The apparatus according to claim 1, wherein the sensing surface comprises a dielectric layer.

10. The apparatus according to claim 6, wherein the detecting unit comprises a polarizer and a photodetector and is adapted to compare the phase of said testing beam and said reference beam.

11. A method for SPR sensing and LRSPR sensing, said method comprising:
(a) generating a phase modulated testing beam and a phase modulated reference beam;
wherein the generating a phase modulated testing beam and a phase modulated reference beam comprises using a liquid crystal modulator to phase modulate said testing beam and said reference beam;
(b) converging said phase modulated testing beam onto said sensing surface;
(c) reflecting said testing beam off a sensing surface of a sample from a plurality of illumination angles; and
(d) comparing the phase in the reflected testing beam against the phase of said reference beam to characterize said sample.

12. The method according to claim 11 wherein said comparing comprises: forming an interference between p- and s-polarization components of the reference beam; and
comparing the phase in said interfered reference beam against the phase of said testing beam.

13. The method according to claim 11 further comprising flowing a sample over the sensing surface.

14. The method according to claim 11 wherein the sensing surface comprises a dielectric layer.

* * * * *